US009370325B2

(12) United States Patent
Al-Ali et al.

(10) Patent No.: US 9,370,325 B2
(45) Date of Patent: Jun. 21, 2016

(54) HEMOGLOBIN DISPLAY AND PATIENT TREATMENT

(71) Applicant: Masimo Corporation, Irvine, CA (US)

(72) Inventors: Ammar Al-Ali, Tustin, CA (US); Massi Joe E. Kiani, Laguna Niguel, CA (US); Michael O'Reilly, Dana Point, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 14/714,691

(22) Filed: May 18, 2015

(65) Prior Publication Data

US 2015/0245793 A1 Sep. 3, 2015

Related U.S. Application Data

(63) Continuation of application No. 14/064,026, filed on Oct. 25, 2013, now Pat. No. 9,037,207, which is a continuation of application No. 12/783,436, filed on May 19, 2010, now Pat. No. 8,571,619.

(60) Provisional application No. 61/180,018, filed on May 20, 2009, provisional application No. 61/221,435, filed on Jun. 29, 2009.

(51) Int. Cl.
| *A61B 5/00* | (2006.01) |
| *A61B 5/145* | (2006.01) |
| *A61M 5/172* | (2006.01) |
| *A61B 5/1455* | (2006.01) |
| *A61M 37/00* | (2006.01) |

(52) U.S. Cl.
CPC .......... *A61B 5/14546* (2013.01); *A61B 5/1455* (2013.01); *A61B 5/14551* (2013.01); *A61B 5/416* (2013.01); *A61B 5/7257* (2013.01); *A61B 5/742* (2013.01); *A61M 5/1723* (2013.01); *A61B 5/14532* (2013.01); *A61B 5/14552* (2013.01); *A61B 5/6826* (2013.01); *A61M 37/00* (2013.01)

(58) Field of Classification Search
CPC ........................................................ A61B 5/14
USPC ........................................................ 600/322
See application file for complete search history.

(56) References Cited

U.S. PATENT DOCUMENTS

| 3,802,776 | A | * | 4/1974 | Tchang | .................. G01N 21/27 250/565 |
| 4,648,028 | A | * | 3/1987 | DeKlotz | ............ G05B 19/4069 345/634 |
| 4,834,532 | A | * | 5/1989 | Yount | .................. A61B 5/1495 250/252.1 |
| 4,843,013 | A | * | 6/1989 | Chiang | .............. A61B 5/14539 436/11 |
| 4,960,128 | A | | 10/1990 | Gordon et al. | |
| 4,964,408 | A | | 10/1990 | Hink et al. | |

(Continued)

OTHER PUBLICATIONS

US 8,845,543, 09/2014, Diab et al. (withdrawn)

*Primary Examiner* — Clayton E Laballe
*Assistant Examiner* — Kevin Butler
(74) *Attorney, Agent, or Firm* — Knobbe Martens Olson & Bear, LLP (57) ABSTRACT

The present disclosure describes embodiments of a patient monitoring system and methods that include the measure and display of hemoglobin statistics. In an embodiment, total hemoglobin trending is displayed over a period of time. Statistics can include frequency domain analysis, which may be unique for each patient monitored. The total hemoglobin trending and/or statistics can further be used to help control the treatment of a patient, such as being used to control IV administration.

20 Claims, 7 Drawing Sheets

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,193,543 A * | 3/1993 | Yelderman ......... A61B 5/14551 356/41 |
| 5,297,548 A * | 3/1994 | Pologe ............... A61B 5/02416 356/41 |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,575,284 A * | 11/1996 | Athan ................ A61B 5/14551 356/41 |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,692,503 A * | 12/1997 | Kuenstner .......... A61B 5/14551 356/41 |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,803,909 A * | 9/1998 | Maki .................... A61B 5/0059 600/310 |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A * | 7/1999 | Diab .................... A61B 5/14551 600/323 |
| 5,934,925 A | 8/1999 | Tobler et al. |
| 5,940,182 A | 8/1999 | Lepper, Jr. et al. |
| 5,957,885 A * | 9/1999 | Bollish ............... A61M 5/1723 604/67 |
| 5,995,855 A | 11/1999 | Kiani et al. |
| 5,997,343 A | 12/1999 | Mills et al. |
| 6,002,952 A | 12/1999 | Diab et al. |
| 6,011,985 A * | 1/2000 | Athan ................ A61B 5/14551 600/322 |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,174,283 B1 * | 1/2001 | Nevo .................... A61B 5/0205 600/301 |
| 6,184,521 B1 | 2/2001 | Coffin, IV et al. |
| 6,206,830 B1 | 3/2001 | Diab et al. |
| 6,223,064 B1 * | 4/2001 | Lynn .................. A61B 5/14551 600/324 |
| 6,229,856 B1 * | 5/2001 | Diab .................. A61B 5/14551 375/316 |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,473,632 B1 * | 10/2002 | Myers ................. A61B 5/1455 600/322 |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,611,320 B1 * | 8/2003 | Lindberg .......... A61B 5/14551 356/40 |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 * | 11/2003 | Diab .................. A61B 5/14551 600/323 |
| 6,650,917 B2 * | 11/2003 | Diab .................. A61B 5/14546 600/323 |
| 6,654,624 B2 | 11/2003 | Diab et al. |
| 6,658,276 B2 * | 12/2003 | Kianl ................. A61B 5/0002 600/322 |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |

(56) References Cited

U.S. PATENT DOCUMENTS

| | | | |
|---|---|---|---|
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,763,256 B2 * | 7/2004 | Kimball | A61B 5/0285 600/336 |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,879,850 B2 * | 4/2005 | Kimball | A61B 5/14551 600/336 |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,763 B2 * | 1/2006 | Boas | G01N 21/314 600/323 |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 * | 5/2007 | Diab | A61B 5/14546 600/310 |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,319,894 B2 * | 1/2008 | Higgins | A61B 5/0075 600/322 |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 * | 3/2008 | Lamego | A61B 5/14551 600/323 |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 * | 5/2009 | Soyemi | G01N 33/4925 600/323 |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |

(56) References Cited

U.S. PATENT DOCUMENTS

| | | |
|---|---|---|
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |

(56) References Cited

U.S. PATENT DOCUMENTS

| | | | |
|---|---|---|---|
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 2004/0034293 A1* | 2/2004 | Kimball ............ A61B 5/14551 600/323 |
| 2004/0034294 A1* | 2/2004 | Kimball ............. A61B 5/0285 600/323 |
| 2004/0122300 A1* | 6/2004 | Boas .................... G01N 21/314 600/323 |
| 2005/0019936 A1* | 1/2005 | Samsoondar .......... B01L 3/508 436/80 |
| 2007/0093701 A1* | 4/2007 | Myers .................. A61B 5/0059 600/323 |
| 2008/0097173 A1* | 4/2008 | Soyemi ............. G01N 33/4925 600/310 |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2009/0326342 A1* | 12/2009 | Huiku ................ A61B 5/14551 600/322 |
| 2010/0004518 A1 | 1/2010 | Vo et al. |
| 2010/0030040 A1 | 2/2010 | Poeze et al. |
| 2010/0099964 A1* | 4/2010 | O'Reilly ............ A61B 5/14546 600/323 |
| 2010/0198029 A1* | 8/2010 | Wang .................... A61B 5/6814 600/323 |
| 2010/0261979 A1 | 10/2010 | Kiani |
| 2010/0298675 A1* | 11/2010 | Al-Ali ................ A61B 5/14551 600/322 |
| 2011/0001605 A1 | 1/2011 | Kiani et al. |
| 2011/0028809 A1* | 2/2011 | Goodman .......... A61B 5/02416 600/322 |
| 2011/0082711 A1 | 4/2011 | Poeze et al. |
| 2011/0105854 A1 | 5/2011 | Kiani et al. |
| 2011/0190613 A1* | 8/2011 | Zhang ................. A61B 5/1455 600/328 |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0029301 A1* | 2/2012 | Battista, Jr. ......... G06F 19/3406 600/300 |
| 2012/0059267 A1 | 3/2012 | Lamego et al. |
| 2012/0116175 A1* | 5/2012 | Al-Ali ................ A61B 5/14542 600/300 |
| 2012/0123231 A1* | 5/2012 | O'Reilly ............ A61B 5/14551 600/340 |
| 2012/0179006 A1* | 7/2012 | Jansen ................. A61B 5/0537 600/301 |
| 2012/0209082 A1 | 8/2012 | Al-Ali |
| 2012/0209084 A1 | 8/2012 | Olsen et al. |
| 2012/0209095 A1* | 8/2012 | Huiku ................ A61B 5/14551 600/322 |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0289797 A1* | 11/2012 | Al-Ali .................... A61B 5/021 600/316 |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |

(56) References Cited

U.S. PATENT DOCUMENTS

| | | |
|---|---|---|
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

\* cited by examiner

HEMOGLOBIN DISPLAY AND PATIENT TREATMENT

REFERENCE TO RELATED APPLICATIONS

This application is a continuation of U.S. patent application Ser. No. 14/064,026, filed Oct. 25, 2013, entitled "Hemoglobin Display and Patient Treatment," which is a continuation of U.S. patent application Ser. No. 12/783,436, filed May 19, 2010, entitled "Hemoglobin Display and Patient Treatment," which claims priority benefit under 35 U.S.C. §119(e) of U.S. Provisional Application Nos. 61/180,018 filed May 20, 2009, entitled "Hemoglobin Display," and 61/221,435 entitled "Hemoglobin Display and Patient Treatment," filed Jun. 29, 2009. The present application incorporates the disclosures of the foregoing applications herein by reference in their entireties.

FIELD OF THE INVENTION

The present disclosure relates to the processing and display of a hemoglobin measurement.

BACKGROUND

During patient care, it is important to know the composition of the patient's blood. Knowing the composition of the patient's blood can provide an indication of the patient's condition, assist in patient diagnosis, and assist in determining a course of treatment. One blood component in particular, hemoglobin, is very important. Hemoglobin is responsible for the transport of oxygen from the lungs to the rest of the body. If there is insufficient total hemoglobin or if the hemoglobin is unable to bind with or carry enough oxygen, then the patient can suffocate. In addition to oxygen, other molecules can bind to hemoglobin. For example, hemoglobin can bind with carbon monoxide to form carboxyhemoglobin. When other molecules bind to hemoglobin, the hemoglobin is unable to carry oxygen molecules, and thus the patient is deprived of oxygen. Also, hemoglobin can change its molecular form and become unable to carry oxygen, this type of hemoglobin is called methemoglobin.

Pulse oximetry systems for measuring constituents of circulating blood have gained rapid acceptance in a wide variety of medical applications including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically at least one emitting a red wavelength and one emitting an infrared (IR) wavelength, and a photodiode detector. The emitters and detector are attached to a patient tissue site, such as a finger. The patient cable transmits drive signals to these emitters from the monitor, and the emitters respond to the drive signals to transmit light into the tissue site. The detector generates a signal responsive to the emitted light after attenuation by pulsatile blood flow within the tissue site. The patient cable transmits the detector signal to the monitor, which processes the signal to provide a numerical readout of physiological parameters such as oxygen saturation (SpO2) and pulse rate.

Standard pulse oximeters, however, are unable to provide an indication of how much hemoglobin is in a patient's blood or whether other molecules were binding to hemoglobin and preventing the hemoglobin from binding with oxygen. Caregivers had no alternative but to measure most hemoglobin parameters, such as total hemoglobin, methemoglobin and carboxyhemoglobin by drawing blood and analyzing it in a lab. Given the nature of non-continuous blood analysis in a lab, it was widely believed that total hemoglobin did not change rapidly.

Advanced physiological monitoring systems utilize multiple wavelength sensors and multiple parameter monitors to provide enhanced measurement capabilities including, for example, the measurement of carboxyhemoglobin (HbCO), methemoglobin (HbMet) and total hemoglobin (Hbt or tHb). Physiological monitors and corresponding multiple wavelength optical sensors are described in at least U.S. patent application Ser. No. 11/367,013, filed Mar. 1, 2006 and titled Multiple Wavelength Sensor Emitters and U.S. patent application Ser. No. 11/366,208, filed Mar. 1, 2006 and titled Noninvasive Multi-Parameter Patient Monitor, both assigned to Masimo Laboratories, Irvine, Calif. ("Masimo Labs") and both incorporated by reference herein. Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and Rad-57™, Rad-87™ and Radical-7™ monitors for measuring SpO2, pulse rate, perfusion index, signal quality, HbCO and HbMet among other parameters are also available from Masimo.

SUMMARY

The present disclosure provides for the measurement, display and analysis of hemoglobin content in living patients. It has been discovered that, contrary to the widely held understanding that total hemoglobin does not change rapidly, total hemoglobin fluctuates over time. In an embodiment, the trend of a patient's continuous total hemoglobin (tHb or Hbt) measurement is displayed on a display. In an embodiment, the trend of the total hemoglobin is analyzed through, for example, a frequency domain analysis to determine patterns in the patient hemoglobin fluctuation. In an embodiment, a frequency domain analysis is used to determine a specific signature of the hemoglobin variability specific to a particular patient. In some embodiments, the specific elements of a patient's hemoglobin variability may provide information useful for the diagnosis of specific diseases, including, for example, diseases that affect hemoglobin and red blood cell function such as sickle cell anemia.

Additionally, exemplary uses of these hemoglobin readings are illustrated in conjunction with dialysis treatment and blood transfusions.

BRIEF DESCRIPTION OF THE DRAWINGS

The drawings and following associated descriptions are provided to illustrate embodiments of the present disclosure and do not limit the scope of the claims. Corresponding numerals indicate corresponding parts, and the leading digit of each numbered item indicates the first figure in which an item is found.

DETAILED DESCRIPTION

Aspects of the disclosure will now be set forth in detail with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit the scope of the disclosure herein, which is instead defined by the claims following this description.

Figure 1:
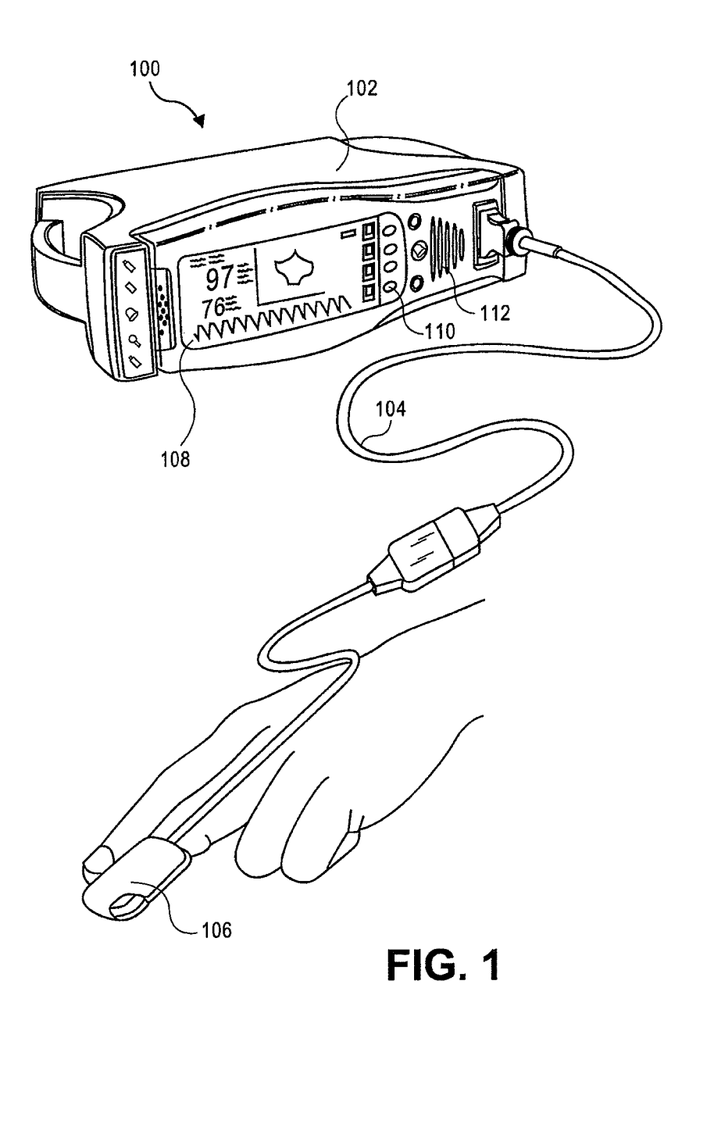
FIG. 1 illustrates a perspective view of a patient monitoring system in accordance with an embodiment of the disclosure.

Turning to FIG. 1, an embodiment of a patient monitoring system 100 is illustrated. The patient monitoring system 100 includes a patient monitor 102 attached to a sensor 106 by a cable 104. The sensor monitors various physiological data of a patient and sends signals indicative of the parameters to the patient monitor 102 for processing. The patient monitor 102 generally includes a display 108, control buttons 110, and a speaker 112 for audible alerts. The display 108 is capable of displaying readings of various monitored patient parameters, which may include numerical readouts, graphical readouts, and the like. Display 108 may be a liquid crystal display (LCD), a cathode ray tube (CRT), a plasma screen, a Light Emitting Diode (LED) screen, Organic Light Emitting Diode (OLED) screen, or any other suitable display. A patient monitoring system 102 may monitor oxygen saturation ($SpO_2$), perfusion index (PI), pulse rate (PR), hemoglobin count, and/or other parameters. An embodiment of a patient monitoring system according to the present disclosure is capable of measuring and displaying total hemoglobin trending data and preferably is capable of conducting data analysis as to the total hemoglobin trending.

Figure 2:
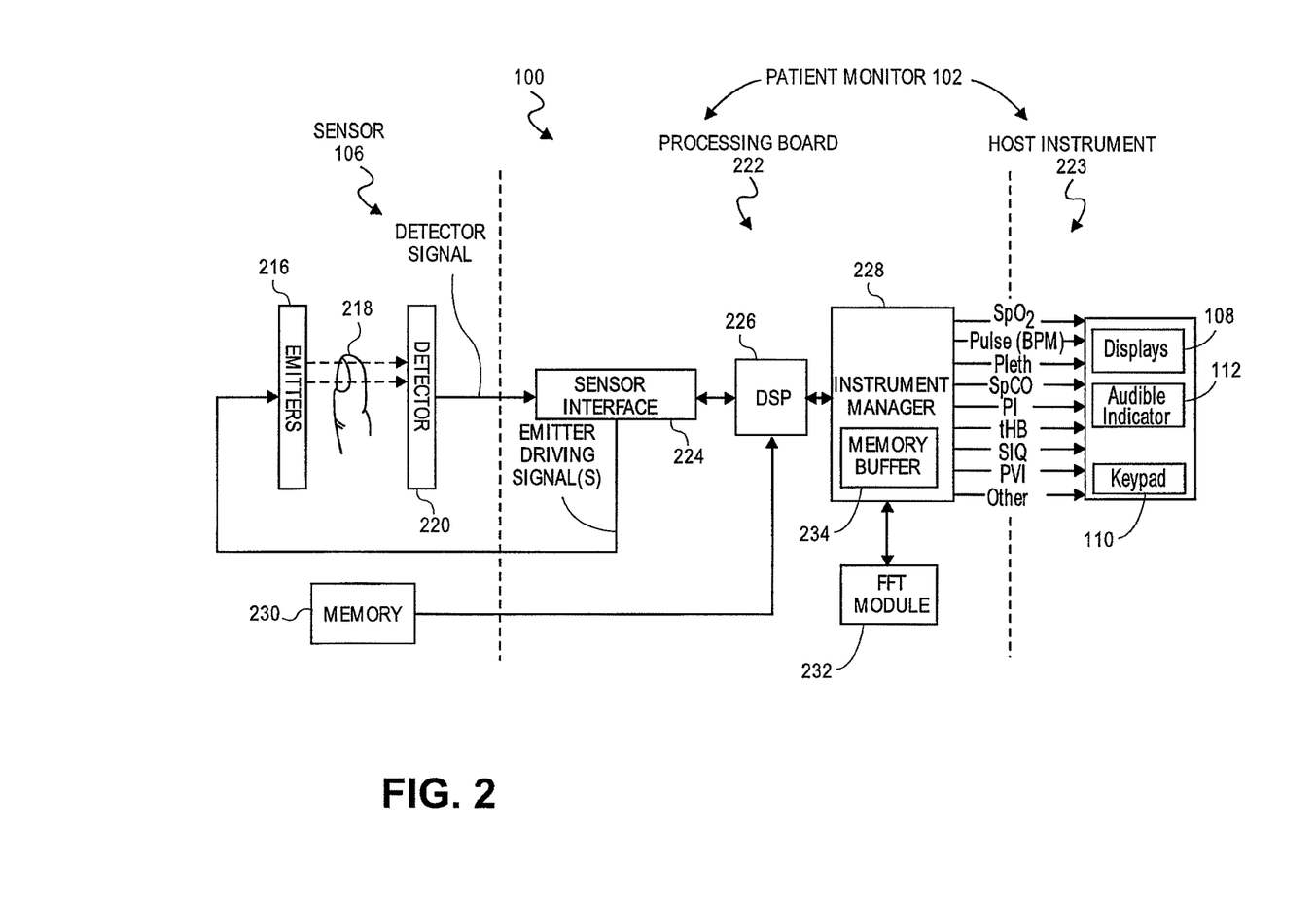
FIG. 2 illustrates a block drawing of a patient monitoring system in accordance with an embodiment of the disclosure.

FIG. 2 illustrates details of an embodiment of a patient monitoring system 100 in a schematic form. Typically a sensor 106 includes energy emitters 216 located on one side of a patient monitoring site 218 and one or more detectors 220 located generally opposite. The patient monitoring site 218 is usually a patient's finger (as pictured), toe, ear lobe, or the like. Energy emitters 216, such as LEDs, emit particular wavelengths of energy through the flesh of a patient at the monitoring site 218, which attenuates the energy. The detector(s) 220 then detect the attenuated energy and send representative signals to the patient monitor 102.

Specifically, an embodiment of the patient monitor 102 includes processing board 222 and a host instrument 223. The processing board 222 includes a sensor interface 224, a digital signal processor (DSP) 226, and an instrument manager 228. In an embodiment of the disclosure, the processing board also includes a fast Fourier transform (FFT) module 232. In an embodiment, the FFT module 232 can comprise a special-purpose processing board or chip, a general purpose processor running appropriate software, or the like. The FFT module 232 may further be incorporated within the instrument manager 228 or be maintained as a separate component (as illustrated in FIG. 2).

The host instrument typically includes one or more displays 108, control buttons 110, a speaker 112 for audio messages, and a wireless signal broadcaster 234. Control buttons 110 may comprise a keypad, a full keyboard, a track wheel, and the like. Additionally embodiments of a patient monitor 102 can include buttons, switches, toggles, check boxes, and the like implemented in software and actuated by a mouse, trackball, touch screen, or other input device.

The sensor interface 224 receives the signals from the sensor 106 detector(s) 220 and passes the signals to the DSP 226 for processing into representations of physiological parameters. These are then passed to the instrument manager 228, which may further process the parameters for display by the host instrument 223. In some embodiments, the DSP 226 also communicates with a memory 230 located on the sensor 106; such memory typically contains information related to the properties of the sensor that may be useful in processing the signals, such as, for example, emitter 216 energy wavelengths. The elements of processing board 222 provide processing of the sensor 106 signals. Tracking medical signals is difficult because the signals may include various anomalies that do not reflect an actual changing patient parameter. Strictly displaying raw signals or even translations of raw signals could lead to inaccurate readings or unwarranted alarm states. The processing board 222 processing generally helps to detect truly changing conditions from limited duration anomalies. The host instrument 223 then is able to display one or more physiological parameters according to instructions from the instrument manager 228, and caregivers can be more confident in the reliability of the readings.

Figure 3:
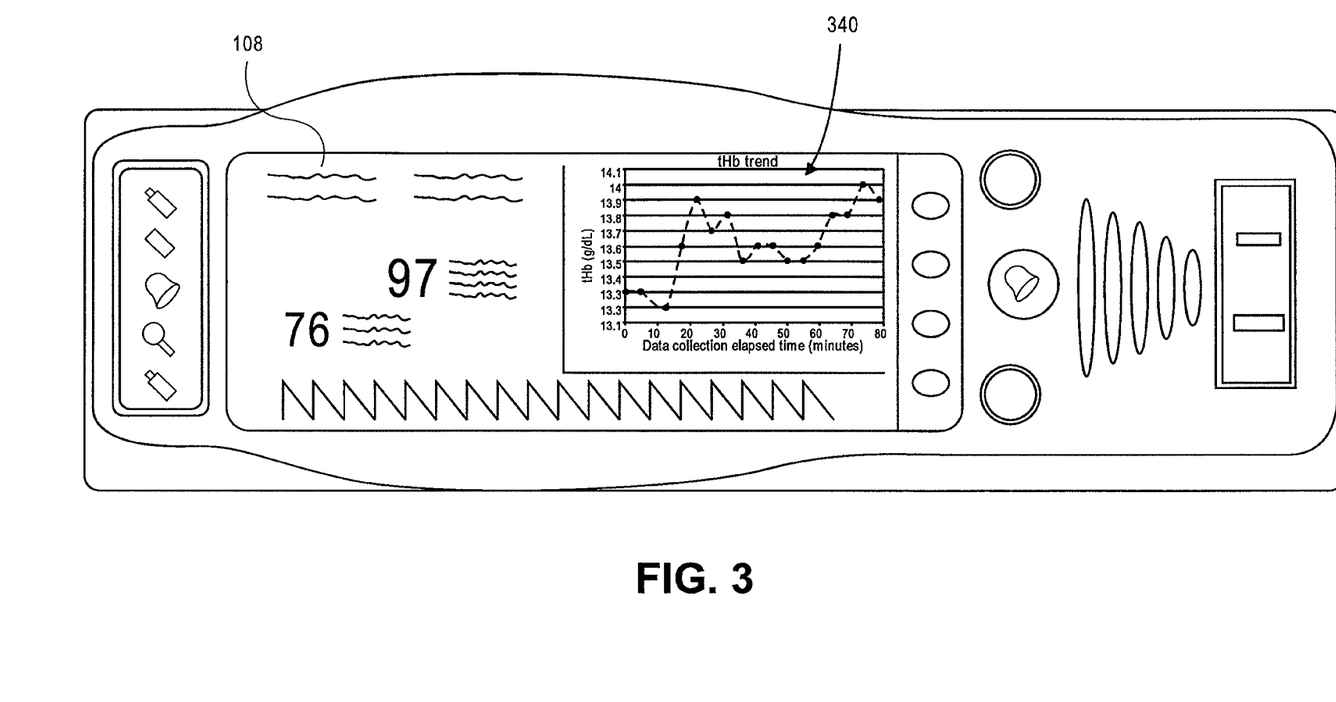
FIG. 3 illustrates a planar view of a patient monitor displaying a sample graph of total hemoglobin versus time as may be displayed by a patient monitoring system in accordance with an embodiment of the disclosure.

In an embodiment, the patient monitor 102 keeps track of total hemoglobin data over a period of time, such as a few minutes, a few hours, a day or two, or the like. It is important to monitor total hemoglobin over a range of time because it has been discovered that hemoglobin fluctuates over time. In an embodiment, the instrument manager may include a memory buffer 234 to maintain this data for processing throughout a period of time. Memory buffer 234 may include RAM, Flash or other solid state memory, magnetic or optical disk-based memories, combinations of the same or the like. The data for total hemoglobin over a period of time can then be passed to host instrument 223 and displayed on display 108. In an embodiment, such a display may include a graph such as that illustrated by FIG. 3. FIG. 3 illustrates a sample tHb trend graph measuring tHb in g/dL over a period of approximately 80 minutes. In an embodiment, a patient monitor 102 may periodically or continuously update the total hemoglobin display to show the previous hour, previous 90 minutes, or some other desirable time period.

Displaying a current total hemoglobin count, as well as data for a prior time period helps allow a caregiver to determine if the current count is within a normal range experienced by the individual patient. It has also been found that the variations in total hemoglobin count are generally cyclic. It is preferable to display a time period that encompasses at least one complete tHb cycle. As such, a caregiver will be quickly able to see if a total hemoglobin count has fallen above or below the patient's general cyclic range. Additionally, the caregiver may also be able to see if the patient's total hemoglobin count is rising or falling abnormally.

Figure 4:
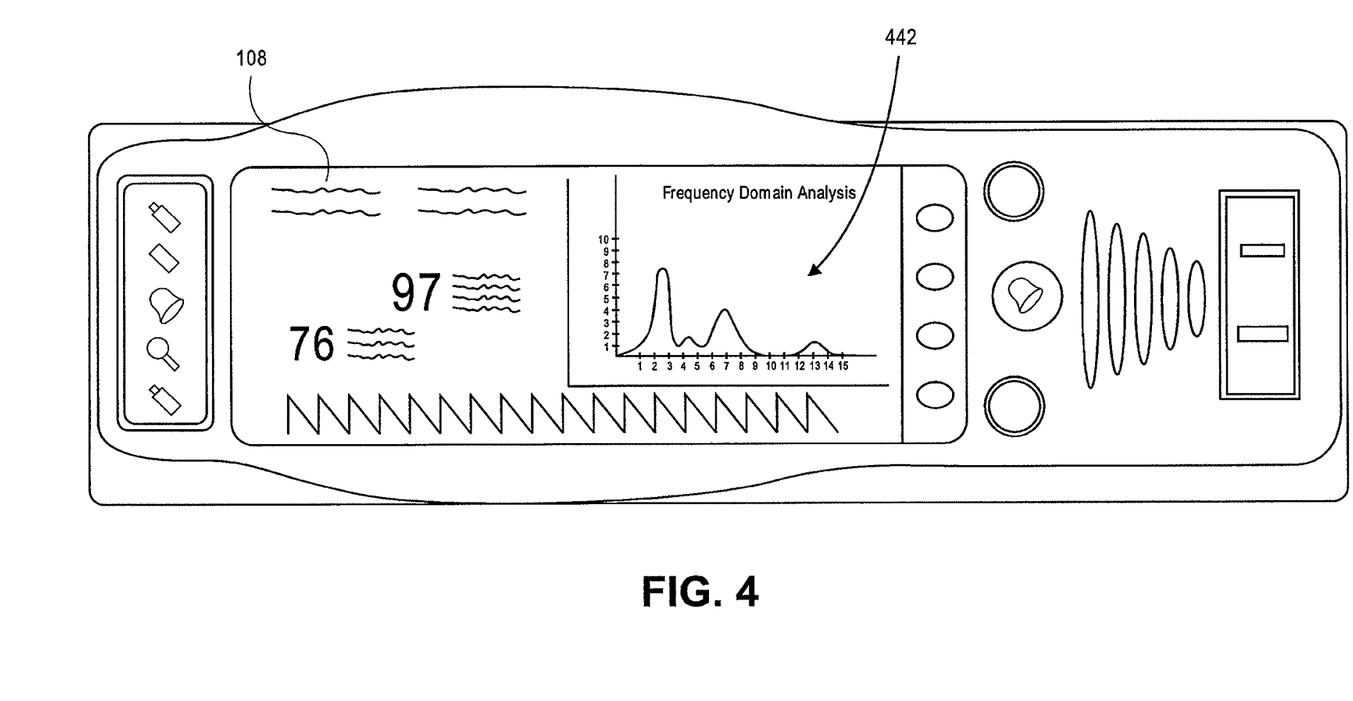
FIG. 4 illustrates a planar view of a patient monitor displaying a graph of a frequency domain analysis.

In an embodiment, the trending of the total hemoglobin is additionally or alternatively analyzed through, for example, a frequency domain analysis to determine patterns in the patient hemoglobin fluctuation. Total hemoglobin data from the instrument manager 228 or its memory buffer 234 is passed to the FFT module 232, in an embodiment, to accomplish such an analysis. The FFT module uses one of a number of fast Fourier transform algorithms to obtain the frequencies of various total hemoglobin readings. The resulting data can be graphed and displayed by the host instrument 223's display(s) 108, as shown by example in FIG. 4.

In an embodiment, both total hemoglobin graphs and frequency domain analysis can be displayed on a single patient monitor display 108. In an embodiment, a button 110 or other control allows switching between two such display states. In other embodiments, the display 108 may change automatically, such as periodically or based on a specific event, such as an abnormal change in a patient's total hemoglobin count.

The frequency domain analysis can determine a specific patient signature for a patient, in an embodiment, because the frequency variations have been found to be unique or semi-unique between different patients. As such, a portion of the memory buffer 234 may maintain a baseline total hemoglobin frequency data set for comparison to later data readings from the sensor 106. Changes in the frequency analysis may indicate a change in a monitored patient's status. In such an embodiment, a baseline reference graph and a more current frequency domain analysis may be graphed together on a single graph display, on multiple proximate graph displays or display windows, or the like to allow caregivers to recognize changes in the patient's hemoglobin levels over time. For example, in an embodiment, a single graph may include both sets of data graphed in different colors, such as a blue baseline reading and a green more current reading frequency analysis. Variations between the two may, in an embodiment, trigger an alert or an alarm if they reach a certain threshold. Such an alert or alarm may be audible and output through audible indicator 112 and/or may alter the display 108. The alarm or alert may incorporate changing colors, flashing portions of a screen, text or audible messages, audible tones, combinations of the same or the like.

Figure 5:
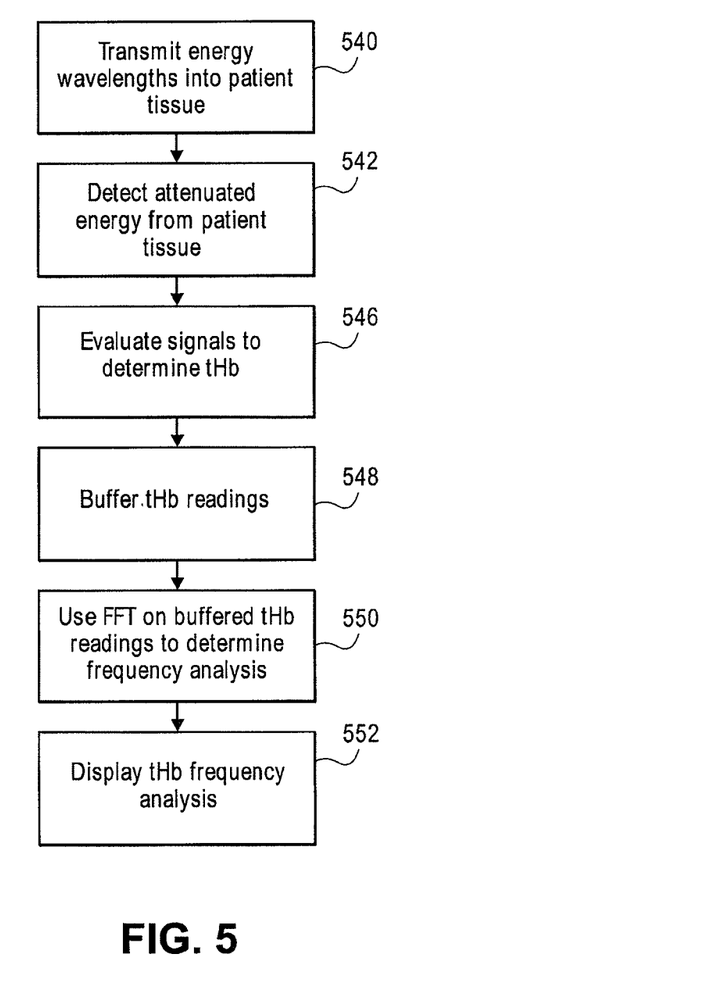
FIG. 5 illustrates a block diagram of a method of monitoring and analyzing a patient's total hemoglobin levels.

FIG. 5 illustrates an embodiment of a method of obtaining, analyzing, and displaying total hemoglobin data for patient status and analysis as generally described herein. Starting with block 540, energy is transmitted through patient tissue at a measurement site, generally by a sensor 106. The patient tissue attenuates the energy which is then detected at block 542. The detected signals are evaluated to determine a current total hemoglobin count (block 546). This step may include, in an embodiment, filtering noise from the signals, filtering errant readings, and the like. In an embodiment, a buffer stores the total hemoglobin readings for a period of time in (block 548). This allows the patient monitor to display trending data, display the total hemoglobin readings for a period of time, rather than just relatively instantaneous readings, and the like. In an embodiment, the patient monitor analyzes the set of buffered total hemoglobin readings using a Fourier transform, such as a discrete Fourier transform, or more preferably one of many suitable fast Fourier transform algorithms (block 550). This analysis decomposes the sequence of total hemoglobin readings into components of different frequencies. Displaying this frequency analysis (block 552) can help caregivers identify changing conditions for a patient that may indicate worsening or improving health conditions.

Figure 6:
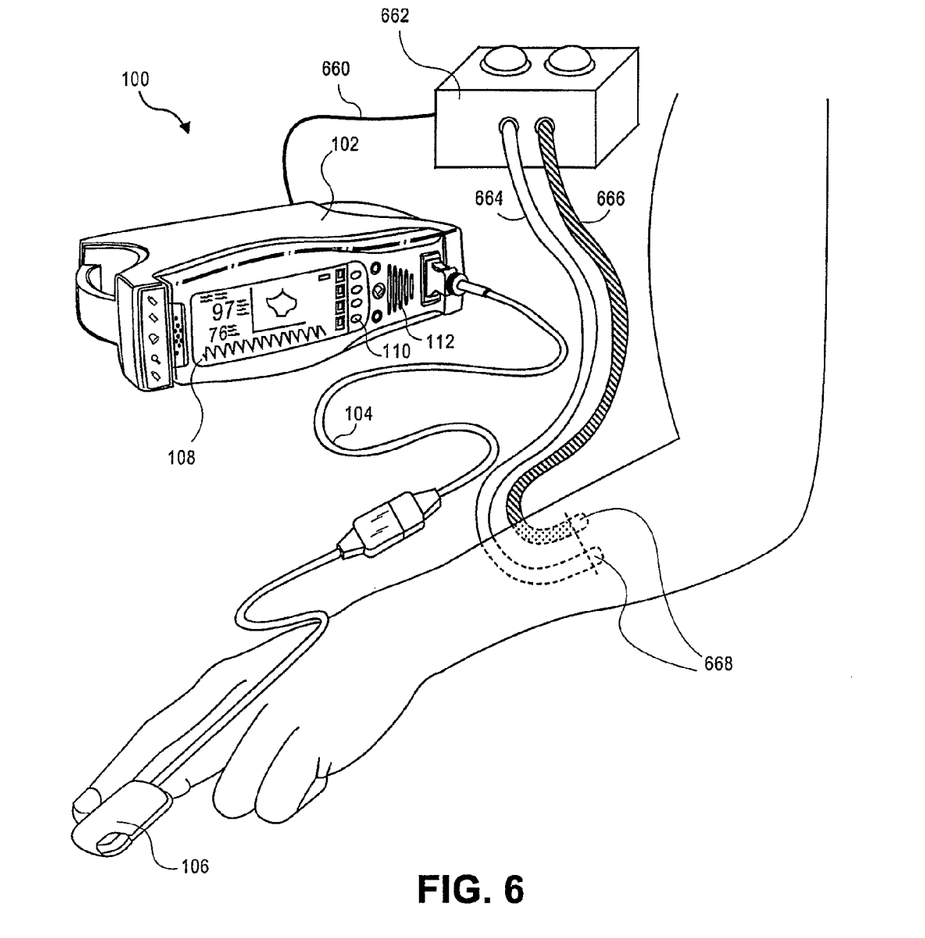
FIG. 6 illustrates a perspective view of a patient monitoring system and blood manipulation device, such as a dialysis machine, in accordance with an embodiment of the disclosure.
Figure 7:
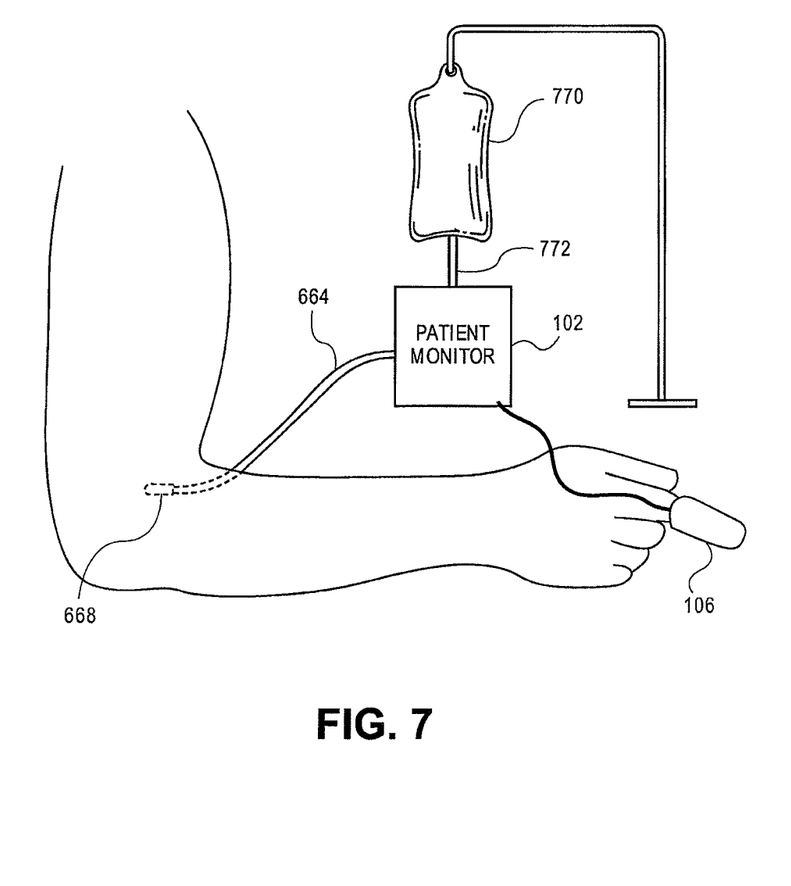
FIG. 7 illustrates a block diagram of a patient monitoring system, including transfusion capabilities in accordance with an embodiment of the disclosure.

The display of trending total hemoglobin data and caregiver understanding of a patient's condition that comes with understanding such a display are important uses. The automatic interpretation of this data into patient care is another. FIGS. 6 and 7 illustrate exemplary systems incorporating uses for patient monitoring of a patient's total hemoglobin in treating the patient for various ailments or injuries. For example, studies have shown that one of the most recurrent problems of hemodialysis is anemia—a condition in which a patient's blood lacks sufficient red blood cells. Dialysis-dependent patients can improve their quality of life by maintaining an adequate hemoglobin level. To this end, it may be advantageous to link the patient monitoring of hemoglobin levels to a dialysis machine to provide hemoglobin level feedback, allowing the dialysis machine to act intelligently and help regulate hemoglobin levels during dialysis. An embodiment of such a system is illustrated in FIG. 6.

As illustrated, an embodiment of the patient monitor 102 is set up in much the same way as described above, with a cable 104 attaching to a noninvasive sensor 106 located proximal to a patient measurement site, such as the finger shown in FIG. 6. An additional cable 660 connects dialysis machine 662 to the patient monitor 102. The dialysis machine 662 generally includes an arterial line 664 and a venous line 664, each of which end in needles 668 for insertion into a patient's artery and vein, respectively. Dialysis machine 662 may then operate at least in part based on hemoglobin levels of the patient as determined by the patient monitor 102. As the hemoglobin levels naturally change, in an embodiment, patient monitor 102 may simply signal the dialysis machine when hemoglobin levels are approaching or have fallen outside of maximum and minimum ranges. Alternatively, the patient monitor 102 may pass hemoglobin level readings to the dialysis machine 662 continuously, at generally periodic intervals, upon changes in hemoglobin level readings, or the like. The dialysis machine 662 can then alter its processing of the blood, inject appropriate amounts of drugs, turn off or on, or otherwise change states or processes based in whole or in part on the hemoglobin levels detected.

FIG. 7 illustrates another exemplary use for patient monitoring of a patient's total hemoglobin in treating the patient for various ailments or injuries. In the embodiment shown, an IV fluid bag is connected to the patient monitor by tubing 772. The patient monitor 102 then incorporates a venous line 664 ending in a needle 668 for insertion into a patient's vein. IVs are often used to administer nutrition, drugs, blood, plasma, and other transfusions, and the like. The patient monitor 102 may thus incorporate a device to control the rate or amount of IV fluid administered to a patient. In the embodiment illustrated, the patient monitor controls the administration, at least in part, based on the hemoglobin levels detected.

As one example, erythropoiesis-stimulating agents (ESAs) are drugs that can help encourage the production of red blood cells. The patient monitor 102 can use the hemoglobin readings of a monitored patient to control the administration of such a drug through an IV. Similarly, the patient monitor can increase the transfusion of blood to a patient if, for example, hemoglobin levels fall below the normal range of hemoglobin. Monitoring the hemoglobin levels with knowledge of the natural fluctuation of those levels in the patient can help reduce the amounts of drugs administered, blood or other fluids transfused, and the like. For example, the patient monitor can help keep the hemoglobin levels in a normal range rather than trying to maintain an exact level, which may lead to less efficient treatment. For example, a falling hemoglobin level may still be within natural limits and may rise without additional treatment. In an embodiment, the patient monitor 102 can withhold treatment in such a situation and provide additional treatment if the hemoglobin is predicted to fall outside or is outside normal limits. This can help reduce the usage of costly treatments and/or conserve those in short supply. Additionally, it may be important to limit usage of a drug due to increased risks of side effects, drug dependency, or the like.

Of course, the foregoing are exemplary only and any IV administered drug, blood, plasma, nutrition, other fluid, or the like that has a tendency to affect hemoglobin levels can be administered and controlled in this manner. One of skill in the art will also understand that the patient monitor and administration devices can be incorporated in a single unit (such as illustrated in FIG. 7) or occur in wired or wirelessly communicating separate units (such as illustrated in FIG. 6) in various embodiments. Administration devices can include not only IV controlling units and dialysis machines as discussed, but other devices designed to aid in providing something of need to a patient. Similarly, other patient parameters detected by sensor 106 and calculated by patient monitor 102 may also be passed to administration devices or used internally to affect the administration of drugs, blood, nutrition, other fluid, or the like.

Hemoglobin concentration can be affected by a variety of different physiological factors, including abnormalities of the hemoglobin or the red blood cells that carry the hemoglobin, vessel fluid volume changes or other physiological factors. For example, fluid volume in the vessel is constantly changing as fluid can enter or exit the blood cell through the arteries. As concentration of hemoglobin is generally determined by the amount of hemoglobin divided by the amount of volume of fluid in the blood cells, changes in the vessel volume will directly affect the hemoglobin concentration. For example, standing up or changing position can alter the hydrostatic affect of blood pressure on the arteries, potentially changing the concentration of total hemoglobin in the blood.

Another exemplary use for patient monitoring of a patient's total hemoglobin involves monitoring these various physiological factors that can affect the total hemoglobin concentration and determining when variations are normal or can indicate physiological problems or abnormalities. For example, in some embodiments differences in the fluid volume based on permeability or other factors that affect the vessel fluid volume can have an effect on the total hemoglobin concentration in the blood. In one embodiment, fluctuations in the permeability of the blood vessels and ion balance can cause the influx our excretion of fluid from the blood vessels causing changes in the hemoglobin concentration. These changes can be normal or periodic changes that can be identified as such through specific algorithms or can be abnormal changes in the permeability that can trigger an alarm during patient monitoring. Also, changes in the rate of hemoglobin production over time can have an effect on the hemoglobin concentration that can be monitored or taken into account. Further, changes in the spleen function, including in its capacity to remove dead or damages red blood cells from the blood stream, can produce changes in the total hemoglobin concentration.

Another exemplary use for patient monitoring of a patient's total hemoglobin related to physiological processes or abnormalities involves determining an abnormality or type of hemoglobin that can be present in the blood. For example, in some embodiments, certain types or deformations of the hemoglobin or red blood cells may cause the total hemoglobin value in a patient's arteries to vary with time or vary locally in certain parts of the arteries. For example, sickle cell anemia, a condition characterized by sickle shaped red blood cells, may cause red blood cells to clump together. This or other abnormalities in the cells may cause local or global variation in the amount of hemoglobin, as a clump of red blood cells may be more dense that a dispersed group of red blood cells, or alter the permeability or ability of the red blood cells to enter the micro circulation. Sometimes, the red blood cells of a person with sickle cell anemia can have difficulty deforming and therefore fitting through vessels in the micro circulation. This can cause them to bunch up near the smaller blood vessels in the micro circulation and change the concentration of hemoglobin. Therefore, this abnormality may exhibit a somewhat normal or predictable cyclical change or frequency of variation in the hemoglobin of the blood and therefore monitoring the total hemoglobin may aid in the diagnosis of these types of conditions. Also, it can cause the hemoglobin concentration to be abnormally low or high in some cases. In other embodiments, various other red blood cell or hemoglobin abnormalities may cause regular variation in the total hemoglobin that may be used to assist in the diagnosis of these ailments, including for example, Thalassemia.

Various data can be collected from patients with hemoglobin and red blood cell abnormalities to determine or identify any potential signatures or unique or predicable fluctuations in the hemoglobin levels. This data can be used to diagnose patients by comparing a patient's hemoglobin variability to that of data from normal patients and from patients with certain abnormalities. This can provide a non-invasive method of screening for certain abnormalities that may otherwise require invasive blood testing by drawing blood and testing it in the lab or other time consuming and costly methods of analysis. Also, knowledge about the physiological processes that cause normal variation in the hemoglobin concentration can increase the ability to screen normal from abnormal variation in the hemoglobin by analyzing total hemoglobin data over time.

For example, in an embodiment, a caregiver can set up the patient monitor 102 to obtain signals from a patient representative of the total hemoglobin of the patient over time. The patient monitor 102 can then send the signals to the processing board 222 to be analyzed and processed to determine whether or not the signals or data from the patient is representative of a patient with a hemoglobin abnormality such as sickle cell anemia or are indicative of normal variation in the hemoglobin concentration. In an embodiment, the signals can be compared to existing data from patients that have been confirmed to have sickle cell anemia to determine if the condition likely exists in the current patient based on similarity of hemoglobin variability. In another embodiment, the signals can be filtered and processed to look for certain signal components that may be indicative of an abnormality such as sickle cell anemia.

Although the foregoing has been described in terms of certain specific embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions, and modifications will be apparent to the skilled artisan in view of the disclosure herein. For example, various functions described as occurring in FFT module 232 may be incorporated within other portions of the processing board 222. Similarly, a patient monitor 102 may not have a distinct processing board 222 and host instrument 223; instead, the various functions described herein may be accomplished by different components within a patient monitor 102 without departing from the spirit of the disclosure. Thus, the present disclosure is not limited by the preferred embodiments, but is defined by reference to the appended claims. The accompanying claims and their equivalents are intended to cover forms or modifications as would fall within the scope and spirit of the disclosure.

What is claimed is:

1. A patient monitoring system comprising:
a noninvasive sensor for emitting energy into a patient measurement site of a patient and detecting the energy attenuated by the patient measurement site;
a memory buffer; and
a hardware processor configured to determine a first plurality of total hemoglobin readings over a first time period using the attenuated energy detected by the sensor and store the first plurality of total hemoglobin readings in the memory buffer,
wherein said hardware processor is further configured to frequency transform the first plurality of total hemoglobin readings stored in the memory buffer,
determine frequency data from the first plurality of total hemoglobin readings; and
determine a hemoglobin characteristic of the patient from the frequency data.

2. The patient monitoring system of claim 1, wherein the hemoglobin characteristic comprises an abnormality.

3. The patient monitoring system of claim 2, wherein the abnormality comprises sickle cell anemia.

4. The patient monitoring system of claim 2, wherein the abnormality comprises Thalasemia.

5. The patient monitoring system of claim 2, wherein the abnormality comprises abnormal spleen function.

6. The patient monitoring system of claim 1, wherein the hemoglobin characteristic comprises a type of hemoglobin.

7. A patient monitoring system comprising:
a hardware processor configured to:
determine a first plurality of total hemoglobin readings over a first time period using the attenuated energy detected by a noninvasive sensor attached to a patient;
store the first plurality of total hemoglobin readings in a memory buffer;
transform the first plurality of total hemoglobin readings stored in the memory buffer in a frequency domain; and
determine a hemoglobin characteristic of the patient based on the transformed total hemoglobin readings.

8. The patient monitoring system of claim 7, wherein the hemoglobin characteristic comprises an abnormality.

9. The patient monitoring system of claim 8, wherein the abnormality comprises sickle cell anemia.

10. The patient monitoring system of claim 8, wherein the abnormality comprises Thalasemia.

11. The patient monitoring system of claim 8, wherein the abnormality comprises abnormal spleen function.

12. The patient monitoring system of claim 8, wherein the hemoglobin characteristic comprises a type of hemoglobin.

13. The patient monitoring method of claim 7, wherein the hardware processor is further configured to control a treatment unit based on the determined hemoglobin characteristic.

14. A patient monitoring method comprising:
emitting energy into a patient measurement site of a patient;
detecting the energy attenuated by the patient measurement site;
determining a first plurality of total hemoglobin readings over a first time period using the attenuated energy detected;
storing the first plurality of total hemoglobin readings in a memory buffer;
transforming the first plurality of total hemoglobin readings stored in the memory buffer in a frequency domain; and
determining a hemoglobin characteristic of the patient based on the transformed total hemoglobin readings.

15. The patient monitoring method of claim 14, wherein the hemoglobin characteristic comprises an abnormality.

16. The patient monitoring method of claim 15, wherein the abnormality comprises sickle cell anemia.

17. The patient monitoring method of claim 15, wherein the abnormality comprises Thalasemia.

18. The patient monitoring method of claim 15, wherein the abnormality comprises abnormal spleen function.

19. The patient monitoring method of claim 15, wherein the hemoglobin characteristic comprises a type of hemoglobin.

20. The patient monitoring method of claim 14, further comprising controlling a treatment unit based on the determined hemoglobin characteristic.

* * * * *